(12) United States Patent
Besso

(10) Patent No.: US 10,595,559 B2
(45) Date of Patent: Mar. 24, 2020

(54) AEROSOL-GENERATING ARTICLE COMPRISING A DETACHABLE FRESHENER DELIVERY ELEMENT WITH HIGH VENTILATION

(71) Applicant: PHILIP MORRIS PRODUCTS S.A., Neuchatel (CH)

(72) Inventor: Clement Besso, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/564,851

(22) PCT Filed: Apr. 28, 2016

(86) PCT No.: PCT/EP2016/059490
§ 371 (c)(1),
(2) Date: Oct. 6, 2017

(87) PCT Pub. No.: WO2016/174137
PCT Pub. Date: Nov. 3, 2016

(65) Prior Publication Data
US 2018/0116277 A1    May 3, 2018

(30) Foreign Application Priority Data
Apr. 30, 2015 (EP) ..................................... 15166040

(51) Int. Cl.
*A24F 11/00* (2006.01)
*A24F 47/00* (2006.01)
(Continued)

(52) U.S. Cl.
CPC .............. *A24D 3/061* (2013.01); *A24D 1/002* (2013.01); *A24D 1/008* (2013.01); *A24D 3/10* (2013.01);
(Continued)

(58) Field of Classification Search
CPC ............... A24D 1/00; A24D 1/02; A24D 1/04
(Continued)

(56) References Cited

U.S. PATENT DOCUMENTS

| | | |
|---|---|---|
| 515,774 A | 3/1894 | Hotz |
| 2,764,154 A | 1/1953 | Murai |

(Continued)

FOREIGN PATENT DOCUMENTS

| | | |
|---|---|---|
| CN | 1271959 | 8/2006 |
| CN | 101808541 | 8/2010 |

(Continued)

OTHER PUBLICATIONS

European Extended Search Report for Application No. 15166040.4 dated Nov. 17, 2015 (6 pages).

(Continued)

*Primary Examiner* — Abdullah A Riyami
*Assistant Examiner* — Thang H Nguyen
(74) *Attorney, Agent, or Firm* — Mueting, Raasch & Gebhardt, P.A.

(57) ABSTRACT

There is provided an aerosol-generating article (10) comprising an aerosol-generating substrate (12) and a mouthpiece (14) secured to a downstream end of the aerosol-generating substrate (12). The mouthpiece (14) comprises at least one segment of filter material (20) and a vented segment (27) downstream of the at least one segment of filter material (20) and comprising at least one freshener delivery element (26). The vented segment (27) comprising the at least one freshener delivery element (26) is detachable from the at least one segment of filter material (20) to decrease the ventilation of the aerosol-generating article (10).

15 Claims, 3 Drawing Sheets

(51) Int. Cl.
*A24D 3/06* (2006.01)
*A24D 1/00* (2020.01)
*A24D 3/10* (2006.01)
*A24F 7/04* (2006.01)
*A61K 8/11* (2006.01)
*A61K 8/34* (2006.01)
*A61K 8/37* (2006.01)
*A61K 8/49* (2006.01)
*A61Q 11/00* (2006.01)

(52) U.S. Cl.
CPC .............. *A24F 7/04* (2013.01); *A24F 47/008* (2013.01); *A61K 8/11* (2013.01); *A61K 8/34* (2013.01); *A61K 8/347* (2013.01); *A61K 8/37* (2013.01); *A61K 8/498* (2013.01); *A61Q 11/00* (2013.01)

(58) Field of Classification Search
USPC .................... 131/328, 275, 337, 335, 280
See application file for complete search history.

(56) References Cited

U.S. PATENT DOCUMENTS

| | | | |
|---|---|---|---|
| 2,893,399 A | 7/1959 | Jacoby | |
| 3,752,165 A | 8/1973 | Harllee | |
| 4,138,477 A | 2/1979 | Gaffar | |
| 4,238,475 A | 12/1980 | Witzel | |
| 4,657,032 A | 4/1987 | Dorr | |
| 4,774,972 A | 10/1988 | Hayes | |
| 4,924,888 A * | 5/1990 | Perfetti | A24D 1/00 131/331 |
| 4,981,522 A * | 1/1991 | Nichols | A24B 15/165 131/194 |
| 5,059,416 A | 10/1991 | Cherukuri | |
| 5,724,997 A * | 3/1998 | Smith | A24D 3/048 131/187 |
| 6,426,089 B1 * | 7/2002 | Sunohara | A61K 8/11 424/400 |
| 7,434,586 B2 | 10/2008 | Higashi | |
| 2007/0074733 A1 * | 4/2007 | Rasouli | A24D 3/04 131/231 |
| 2007/0095357 A1 | 5/2007 | Besso | |
| 2007/0267033 A1 * | 11/2007 | Mishra | A24B 15/283 131/275 |
| 2008/0302376 A1 | 12/2008 | Karles | |
| 2009/0007925 A1 * | 1/2009 | Rasouli | A24D 3/04 131/275 |
| 2010/0108084 A1 * | 5/2010 | Norman | A24D 1/02 131/338 |
| 2011/0100384 A1 * | 5/2011 | Newbery | A24B 15/282 131/282 |
| 2011/0155151 A1 * | 6/2011 | Newman | A24F 47/008 131/275 |
| 2011/0232659 A1 * | 9/2011 | Ercelebi | A24D 3/0216 131/280 |
| 2012/0017925 A1 * | 1/2012 | Sebastian | A24D 1/02 131/332 |
| 2012/0017927 A1 * | 1/2012 | Kobal | A24B 15/283 131/337 |
| 2012/0037172 A1 * | 2/2012 | Allen | A24D 3/061 131/275 |
| 2013/0180534 A1 * | 7/2013 | Shen | A24B 15/282 131/275 |
| 2014/0305455 A1 * | 10/2014 | Crooks | A24D 1/02 131/332 |
| 2015/0027477 A1 | 1/2015 | Kobayashi | |

FOREIGN PATENT DOCUMENTS

| | | |
|---|---|---|
| CN | 203015829 | 6/2013 |
| CN | 103932392 | 7/2014 |
| CN | 104219972 | 12/2014 |
| DE | 1873551 U | 6/1963 |
| EP | 0793420 | 3/2000 |
| EP | 1336346 | 8/2003 |
| JP | 2008024696 | 2/2008 |
| JP | 5183104 | 1/2013 |
| RU | 86083 | 8/2009 |
| RU | 121426 | 10/2012 |
| TW | 200806208 | 2/2008 |
| WO | WO 98/07338 | 2/1998 |
| WO | WO 2010/115829 | 10/2010 |
| WO | WO 2013/178515 | 12/2013 |
| WO | WO 2014/049494 | 4/2014 |

OTHER PUBLICATIONS

Leffingwell, John C., "Cooling Ingredients and Their Mechanism of Action", reprinted from Handbook of Cosmetic Science and Technology, 3$^{rd}$ ed., 2009, pp. 661-675.
International Search Report and Written Opinion for PCT/EP2016/059490 dated Jul. 13, 2016 (10 pages).
Office Action issued in Russia for Application No. 201734804 dated Sep. 27, 2019 (14 pages). English translation included.
Office Action issued in Taiwan for Application No. 105111439 dated Sep. 20, 2019 (3 pages). English translation included.
Office Action issued in China for Application No. 201680022407.1 dated Dec. 12, 2019 (13 pages). English translation included.

* cited by examiner

AEROSOL-GENERATING ARTICLE COMPRISING A DETACHABLE FRESHENER DELIVERY ELEMENT WITH HIGH VENTILATION

This application is a U.S. National Stage Application of International Application No. PCT/EP2016/059490, filed Apr. 28, 2016, which was published in English on Nov. 3, 2016, as International Publication No. WO 2016/174137 A1. International Application No. PCT/EP2016/059490 claims priority to European Application No. 15166040.4 filed Apr. 30, 2015.

The present invention relates to an aerosol-generating article comprising a detachable freshener delivery element. The invention finds particular application as an elongate smoking article, such as a cigarette.

After smoking a smoking article, such as a cigarette, it is common for a consumer to utilise a post-smoking breath freshener. One example of a common breath freshener is a liquid breath freshener composition that carried in a container and sprayed into the consumer's mouth after smoking. Other known breath fresheners include chewable breath fresheners, such as mentholated sweets and chewing gum. However, some consumers may find it inconvenient to carry a separate breath freshener.

Alternative attempts at providing a freshening sensation to a consumer include the addition of menthol into the cigarette itself. However, delivering menthol via the mainstream smoke during smoking of the cigarette often provides an inadequate delivery of menthol to the consumer when compared with breath freshener products such as sprays and chewable breath fresheners that are inserted directly into the mouth.

Therefore, it would be desirable to provide a novel breath freshener for consumers of aerosol-generating articles that mitigates or overcomes the disadvantages of known breath freshener delivery systems.

According to the present invention there is provided an aerosol-generating article comprising an aerosol-generating substrate and a mouthpiece secured to a downstream end of the aerosol-generating substrate. The mouthpiece comprises at least one segment of filter material and a vented segment downstream of the at least one segment of filter material and comprising at least one freshener delivery element. The vented segment comprising the at least one freshener delivery element is detachable from the at least one segment of filter material to decrease the ventilation of the aerosol-generating article.

As used herein, the terms "upstream" and "downstream" are used to describe the relative positions of elements, or portions of elements, of the aerosol-generating article in relation to the direction in which a consumer draws on the aerosol-generating article during use thereof. Aerosol-generating articles as described herein comprise a downstream end (that is, the mouth end) and an opposed upstream end. In use, a consumer draws on the downstream end of the aerosol-generating article. The downstream end is downstream of the upstream end, which may also be described as the distal end.

As used herein, the term 'aerosol-generating substrate' is used to describe a substrate capable of releasing, upon heating, volatile compounds, which can form an aerosol. The aerosol generated from aerosol-generating substrates may be visible or invisible and may include vapours (for example, fine particles of substances, which are in a gaseous state, that are ordinarily liquid or solid at room temperature) as well as gases and liquid droplets of condensed vapours.

As used herein, the term 'vented segment' refers to a removable segment that provides high ventilation of the mouthpiece. After the vented segment has been removed, one or more of the remaining mouthpiece segments may be ventilated, but any ventilation provided by the remaining mouthpiece segments is lower than the ventilation of the vented segment.

As used herein, the term 'freshener delivery element' refers to an element of the aerosol-generating article which can be used to deliver a breath freshening experience to a consumer, separate from smoking the article. That is, the freshener delivery element is not used to flavour the smoke or other aerosol generated by the article during smoking.

By providing the freshener delivery element as an integral but detachable part of the aerosol-generating article, aerosol-generating articles in accordance with the present invention provide a convenient way for a consumer to carry the freshener delivery element. In particular, the present invention eliminates the need for a consumer to carry a separate freshener delivery element that might be used for post-smoking breath freshening, such as chewing gum.

Furthermore, providing the freshener delivery element as a detachable portion of the aerosol-generating article allows the user to remove the freshener delivery element from the aerosol-generating article prior to smoking, and subsequently administer the freshener directly into the mouth, typically after smoking. Therefore, aerosol-generating articles according to the present invention provide improved breath freshening when compared to known aerosol-generating articles in which a flavourant is delivered during smoking in the mainstream smoke.

The vented segment comprising the freshener delivery element can provide a relatively high amount of ventilation when the vented segment is attached to the aerosol-generating article, which advantageously provides a reminder to the consumer that the freshener delivery element is still attached to the aerosol-generating article if the consumer attempts to smoke the aerosol-generating article without detaching the vented segment comprising the freshener delivery element. In those embodiments in which the aerosol-generating substrate comprises a combustible substrate, such as tobacco, the high amount of ventilation provided by the vented segment can also make it more difficult to light the aerosol-generating article when the vented segment comprising the freshener delivery element remains attached, therefore further reminding the consumer to detach the vented segment prior to smoking the aerosol-generating article.

Preferably, the ventilation of the aerosol-generating article when the vented segment is attached is at least about 90 percent, more preferably at least about 91 percent, more preferably at least about 92 percent, more preferably at least about 93 percent, more preferably at least about 94 percent, more preferably at least about 95 percent. Providing such a high degree of ventilation when the vented segment is attached to the aerosol-generating article maximises the effect of the ventilation as a reminder to the consumer to detach the vented segment comprising the freshener delivery element before smoking the aerosol-generating article, particularly in those embodiments in which the aerosol-generating substrate comprises a combustible material, in which case the very high ventilation may make it difficult to light the aerosol-generating article as most of the air drawn through the mouthpiece enters the aerosol-generating article through the vented segment and therefore bypasses the aerosol-generating substrate.

Preferably, the ventilation of the aerosol-generating article when the vented segment has been detached is less than about 90 percent, more preferably less than about 89 percent, more preferably less than about 88 percent, more preferably less than about 87 percent, more preferably less than about 86 percent, more preferably less than about 85 percent. Providing ventilation within these ranges can provide a more conventional smoking experience for the consumer, after the vented segment has been detached from the aerosol-generating article.

Ventilation of the aerosol-generating article, both before and after the vented segment has been detached, is measured in accordance with ISO 9512:2002.

The resistance to draw of the aerosol-generating article when the vented segment is attached may be substantially the same as the resistance to draw of the aerosol-generating article after the vented segment has been detached. However, to provide a further indication to the consumer of the need to detach the vented segment comprising the freshener delivery element in the event that the consumer attempts to draw on the aerosol-generating article with the vented segment attached, the aerosol-generating article may have a low resistance to draw when the vented segment is attached to the aerosol-generating article and a higher resistance to draw after the vented segment has been detached. That is, detaching the vented segment may result in an increase in the resistance to draw of the aerosol-generating article.

When the vented segment comprising the freshener delivery element is attached, preferably the aerosol-generating article has a resistance to draw of less than about 30 millimeters of water gauge (mmWG), more preferably less than about 20 mmWG, more preferably less than about 10 mmWG, more preferably less than about 5 mmWG, most preferably about zero. A resistance to draw of less than about 30 mmWG will typically be noticed by a consumer as unusually low and may therefore provide a reminder to the consumer to detach the vented segment comprising the freshener delivery element.

Additionally, or alternatively, the aerosol-generating article may have a resistance to draw similar to that of a conventional aerosol-generating article, after the vented segment has been detached. After the vented segment has been detached, preferably the aerosol-generating article has a resistance to draw of between about 40 mmWG and about 150 mmWG, more preferably between about 70 mmWG and about 120 mmWG, more preferably between about 80 mmWG and about 110 mmWG, most preferably between about 95 mmWG and about 105 mmWG.

As used herein, the term "resistance-to-draw" refers to the pressure required to force air through the full length of the object under test at the rate of 17.5 milliliters per second at 22 degrees Celsius and 101 kilopascals (760 Torr). Resistance to draw is expressed in units of millimeters water gauge (mmWG) and is measured in accordance with ISO 6565:2011.

In any of the embodiments described above, the aerosol-generating article may further comprise a wrapper circumscribing the mouthpiece and a portion of the downstream end of the aerosol-generating substrate.

Preferably, the wrapper comprises at least one ventilation hole for admitting ambient air through the wrapper and into the vented segment if the consumer draws on the aerosol-generating article with the vented segment attached. Preferably, the at least one ventilation hole comprises a line of ventilation holes extending around at least a portion of the wrapper.

The wrapper preferably comprises a line of weakness extending around at least a portion of the wrapper so that the vented segment comprises the freshener delivery element is detachable from the aerosol-generating article by breaking the wrapper along the line of weakness. For example, to detach the vented segment a consumer may twist the vented segment relative to the at least one segment of porous filter material to tear the wrapper along the line of weakness.

The line of weakness is preferably a line of perforations extending around the wrapper, preferably a line of micro laser perforations. Preferably, the perforations are spaced at between 10 and 20 perforations per centimeter, more preferably about 15 perforations per centimeter. Typically, the wrapper is pre-perforated prior to being wrapped around the vented segment and the at least one segment of filter material.

In those embodiments in which the wrapper comprises a line of ventilation holes and a line of weakening, the line of ventilation holes and the line of weakness may be separate. Preferably, the line of ventilation holes forms the line of weakness.

In some embodiments, the line of weakness overlies an upstream edge of the vented segment. That is, when the vented segment is detached from the aerosol-generating article, the upstream edge of the removed portion of the wrapper is aligned with the upstream edge of the vented segment in the longitudinal direction.

The term "longitudinal direction" is used herein to refer to the direction extending between the upstream and downstream ends of the aerosol-generating article. Where the aerosol-generating article has a substantially cylindrical shape, the axis of the cylinder extends in the longitudinal direction. The "transverse direction" extends perpendicular to the longitudinal direction, and the "circumferential direction" extends around the longitudinal direction.

In those embodiments in which the line of weakness overlies an upstream edge of the vented segment, an upstream end of the vented segment may abut a downstream end of the at least one segment of filter material. In such embodiments, the downstream edge of the remaining wrapper is aligned with the downstream edge of the at least one segment of filter material at the mouth end of the aerosol-generating article.

Alternatively, the upstream end of the vented segment may be spaced apart from the downstream end of the at least one segment of filter material so that, when the vented segment is detached, the downstream edge of the remaining wrapper is positioned downstream of the downstream edge of the at least one filter segment. That is, the remaining portion of the wrapper upstream of the line of weakness extends downstream of a downstream edge of the at least one segment of filter material so that the portion of the wrapper upstream of the line of weakness defines a mouth end recess when the vented segment has been detached.

In a further alternative, the line of weakness may overlie the vented segment downstream of an upstream edge of the vented segment. In such embodiments, when the vented segment is detached, the remaining portion of the wrapper upstream of the line of weakness extends downstream of a downstream edge of the at least one segment of filter material so that the portion of the wrapper upstream of the line of weakness defines a mouth end recess when the vented segment has been detached.

In those embodiments in which the remaining wrapper forms a mouth end recess after the vented segment has been detached, the wrapper is preferably a tipping paper having a basis weight of between about 65 grams per square meter and about 85 grams per square meter, more preferably between about 70 grams per square meter and about 80 grams per square meter. Additionally, or alternatively, the thickness of the tipping paper may be between about 90 micrometers and about 120 micrometers.

Alternatively, in those embodiments in which the tipping paper is not required to form a mouth end recess after the vented segment has been detached, the tipping paper may have a basis weight of between about 10 grams per square meter and about 100 grams per square meter, more preferably between about 20 grams per square meter and about 80 grams per square meter. The tipping paper may have a basis weight of between about 30 grams per square meter and about 60 grams per square meter, or between about 20 grams per square meter and about 40 grams per square meter. The tipping paper may have a basis weight of about 25 grams per square meter.

In any of the embodiments described above, the aerosol-generating article may further comprise at least one indicia provided on an outer surface of the aerosol-generating article, the at least one indicia providing a further reminder to the consumer of the need to detach the segment of porous material from the aerosol-generating article prior to smoking. The at least one indicia may comprise at least one of text and one or more graphics. For example, in those embodiments in which the aerosol-generating article includes a wrapper comprising a line of weakness, the at least one indicia may comprise a text based message instructing the consumer to tear the wrapper along the line of weakness. Additionally, or alternatively, the at least one indicia may comprise a graphic indicating the location of the line of weakness. The indicia is preferably provided on the wrapper and adjacent the line of weakness. The indicia may be printed or otherwise provided on the outer surface of the wrapper.

The vented segment preferably comprises a segment of support material in which the freshener delivery element is provided. Preferably, the segment of support material comprises one or more ventilation channels formed in a surface of the segment of support material. In those embodiments in which the aerosol-generating article comprises a wrapper comprising at least one ventilation hole, preferably the one or more ventilation channels extend between the at least one ventilation hole and the downstream end of the segment of support material. Preferably, the segment of support material is substantially cylindrical, wherein the one or more ventilations channels are provided in the curved surface of the substantially cylindrical segment of support material to form a fluted cylinder.

The one or more ventilation channels may extend in a spiral manner around a longitudinal axis of the segment of support material. Alternatively, the one or more ventilation channels may extend substantially parallel to the longitudinal axis of the segment of support material. The one or more ventilation channels may have a cross sectional area of at least about 1 square millimeter, at least about 4 square millimeters, or at least about 8 square millimeters. Additionally, or alternatively, the one or more ventilation channels may have a cross section area of less than about 10 square millimeters, less than about 8 square millimeters, less than about 6 square millimeters, or less than about 2 square millimeters. If the cross sectional area is too large, the structural integrity of the segment of support material may be compromised. In some embodiments, the height of the one or more ventilation channels may be from about 0.1 millimeters to about 1 millimeter, such as from about 1.5 millimeters to about 2 millimeters. Additionally, or alternatively, the width of the one or more ventilation channels may be from about 1.5 millimeters to about 3 millimeters, such as from about 4 millimeters to about 6 millimeters.

WO-2014/049494-A1, U.S. Pat. No. 3,752,165-A and U.S. Pat. No. 4,774,972-A describe various methods and materials for forming smoking article segments comprising channels in an outer surface, which may be suitable for forming a segment of support material for use in forming the vented segment of aerosol-generating articles according to the present invention.

In those embodiments in which the vented segment comprises a segment of support material in which the freshener delivery element is provided, the vented segment may have an annular shape defining a channel extending through at least part of the vented segment between an upstream end of the segment and a downstream end of the segment, and wherein the at least one freshener delivery element is contained within the channel extending through at least part of the vented segment. The channel may be open at both ends so that the channel extends from the upstream end of the segment of support material to the downstream end of the segment of support material. Alternatively, the channel may be open only at one end of the segment of support material, so that the channel forms a pocket in which the freshener delivery element is provided. In those embodiments in which the channel comprises only one open end, the open end may be provided at the downstream end of the segment of support material so that the freshener delivery element is visible when the vented segment is attached to the aerosol-generating article, which may provide a visual reminder to the consumer of the need to detach the vented segment. Alternatively, the open end of the channel may be provided at the upstream end of the segment of support material so that the freshener delivery element is only accessible after the vented segment has been detached, which may prevent the freshener delivery element being accidentally and prematurely dislodged from the segment of support material.

Providing a channel through at least part of the segment of support material and in which the freshener delivery element is provided facilitates the manufacture of the aerosol-generating article by permitting insertion of the freshener delivery element into the channel after the segment of support material and the freshener delivery element have been formed separately. In those embodiments in which the channel comprises an open end at the downstream end of the segment of support material, the freshener delivery element can be inserted into the channel in the segment of support material after the segment of support material has been combined with the at least one segment of filter material and the aerosol-generating substrate to form the remainder of the aerosol-generating article. In such embodiments, the vented segment is formed when the freshener delivery element is inserted into the segment of support material.

Providing the freshener delivery element within a channel extending through at least part of the segment of support material also provides a convenient means for the consumer to extract the freshener delivery element from the segment of support material after smoking the aerosol-generating article, or to extract a freshener from the freshener delivery element. For example, in those embodiments in which the freshener delivery element comprises a breakable capsule containing a liquid or gel freshener, the consumer can squeeze the segment of support material to break the capsule and squeeze the freshener along the channel and out of the segment of support material. In such embodiments, the channel preferably comprises an open end at only one end of the segment of support material. Alternatively, the consumer can squeeze the segment of support material to squeeze the entire freshener delivery element along the channel and out of the segment of support material, which may be particularly convenient in those embodiments in which the freshener delivery element comprises a solid, chewable freshener delivery element, for example.

In those embodiments in which the segment of support material has an annular shape and comprises a channel in which the freshener delivery element is contained, each of the channel and the freshener delivery element may have a substantially circular cross-sectional shape. In such embodiments, an internal diameter of the channel is preferably less than an external diameter of the freshener delivery element, which advantageously provides an interference fit between the segment of support material and the freshener delivery element to reduce the risk of the freshener delivery element becoming accidentally dislodged from the segment of support material.

In any of the embodiments described above in which the vented segment comprises a segment of support material, the support material may comprise at least one of cellulose acetate, cellulose, reconstituted cellulose, polylactic acid, polyvinyl alcohol, nylon, polyhydroxybutyrate, a thermoplastic material such as starch, non-woven materials, longitudinally oriented fibres and randomly oriented fibres, paper, crepe, cotton, hemp, flax, and combinations thereof. In one embodiment, the support material comprises a hollow acetate tube formed from low density cellulose acetate.

In any of the embodiments described above, the at least one freshener delivery element may comprise at least one solid freshener delivery element. For example, the freshener delivery element may comprise at least one of a dissolvable or chewable tablet, or chewing gum. Examples of methods and formulations for forming chewing gum are described in U.S. Pat. No. 4,238,475-A and U.S. Pat. No. 5,059,416-A. U.S. Pat. No. 4,138,477-A describes formulations for forming lozenges, pressed candy and tablets each containing a breath freshening formulation.

Additionally, or alternatively, the freshener delivery element may comprise at least one breakable capsule containing a gel or liquid freshener. Examples of breath freshening products containing a liquid or gel breath freshening composition are described in JP-5183104-B2 and EP-0793420-B1.

In any of the embodiments described above, the freshener delivery element may comprise at least one flavourant comprising at least one of menthol, linalool, thymol, eucalyptol, methyl salicylate, and combinations thereof. Additionally, or alternatively, the at least one flavourant may comprise at least one of lemon oil, peppermint oil, parsley oil, champignon essence, green tea extract, oolong tea extract, mugwort drawing-extract, apple extract, kaki-fruit extract, ginger essence, and combinations thereof. Suitable flavourants are described in U.S. Pat. No. 6,426,089-B1.

The at least one flavourant may comprise a diluent. The diluent may comprise at least one of palm oil and a medium-chain triglyceride.

Many naturally occurring flavourants can be obtained either by extraction from a natural source or by chemical synthesis if the structure of the compound is known. The flavourants can be extracted from a part of a plant or an animal by physical means, by enzymes, or by water or an organic solvent, and thus include any extractive, essence, hydrolysate, distillate, or absolute thereof. Plants that can be used to provide flavourants include, but are not limited to, those belonging to the families, Lamiaceae (for example, mints), Apiaceae (for example, anise, fennel), Lauraceae (for example, laurels, cinnamon, rosewood), Rutaceae (for example, citrus fruits), Myrtaceae (for example, anise myrtle), and Fabaceae (for example, liquorice). Non-limiting examples of sources of flavourants include mints such as peppermint and spearmint, coffee, tea, cinnamon, clove, ginger, cocoa, vanilla, chocolate, eucalyptus, geranium, agave, juniper, lemon balm, basil, cinnamon, lemon basil, chive, coriander, lavender, sage, tea, thyme and caraway. The term "mints" is used to refer to plants of the genus *Mentha*. Suitable types of mint leaf may be taken from plant varieties including but not limited to *Mentha piperita, Mentha arvensis, Mentha niliaca, Mentha citrata, Mentha spicata, Mentha spicata crispa, Mentha cordifolia, Mentha longifolia, Mentha pulegium, Mentha suaveolens*, and *Mentha suaveolens* variegate.

The freshener delivery element may provide one or more sensory effects other than a flavour sensation, such as a cooling or a warming sensation, a tingling sensation, a numbing sensation, effervescence, increased salivation, and combinations thereof. These sensory effects may be provided by one or more flavourants, including the flavourants listed above. Additionally, or alternatively, the freshener delivery element may comprise at least one non-flavourant material which provides one or more of these sensory effects without providing a flavour sensation. For example, suitable compounds that produce a cooling effect and can be used as an active material include, but are not limited to, the family of carboxamide compounds, such as the Wilkinson-Sword (WS) compounds WS-3 (N-Ethyl-p-menthane-3-carboxamide), WS-23 (2-Isopropyl-N,2,3-trimethylbutyramide), WS-5 [Ethyl 3-(p-menthane-3-carboxamido)acetate], WS-27 (N-Ethyl-2,2-diisopropylbutanamide), WS-14 [N-([ethoxycarbonyl]methyl)-p-menthane-3-carboxamide], and WS-116 (N-(1,1-Dimethyl-2-hydroxyethyl)-2,2-diethylbutanamide).

Aerosol-generating articles according to the present invention may be filter cigarettes or other aerosol-generating articles in which the aerosol-generating substrate comprises a tobacco material that is combusted to form smoke. Therefore, in any of the embodiments described above, the aerosol-generating substrate may comprise a tobacco rod.

Alternatively, aerosol-generating articles according to the present invention may be articles in which a tobacco material is heated to form an aerosol, rather than combusted. In one type of heated aerosol-generating article, a tobacco material is heated by one or more electrical heating elements to produce an aerosol. In another type of heated aerosol-generating article, an aerosol is produced by the transfer of heat from a combustible or chemical heat source to a physically separate tobacco material, which may be located within, around or downstream of the heat source. The present invention further encompasses aerosol-generating articles in which a nicotine-containing aerosol is generated from a tobacco material, tobacco extract, or other nicotine source, without combustion, and in some cases without heating, for example through a chemical reaction.

The invention will now be further described, by way of example only, with reference to the accompanying drawings in which.

Figure 1:
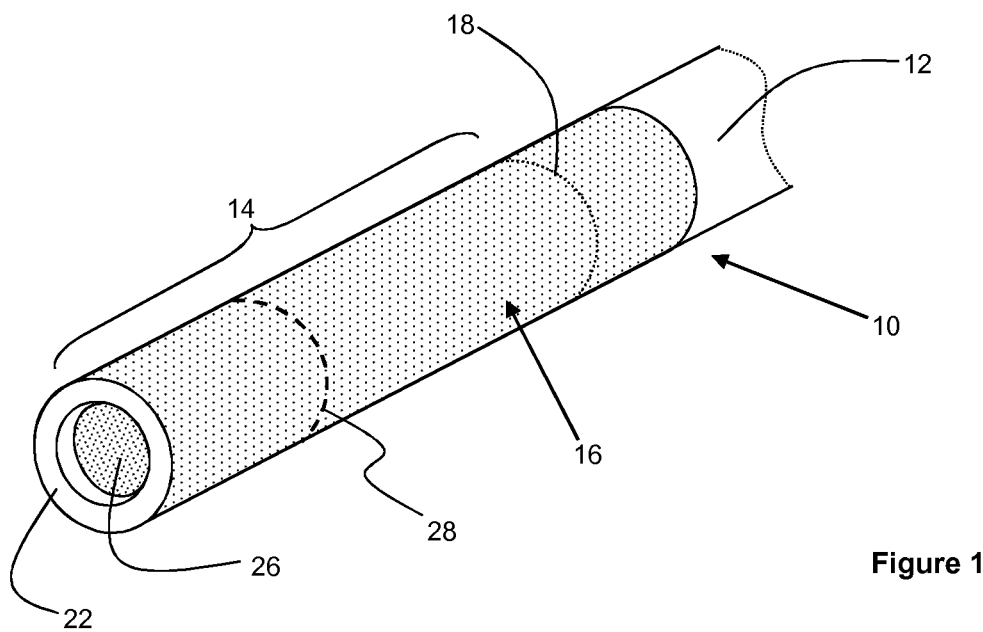
FIG. 1 shows a perspective view of an aerosol-generating article in accordance with a first embodiment of the present invention.

FIG. 1 shows an aerosol-generating article 10 in accordance with a first embodiment of the present invention. The aerosol-generating article 10 is a smoking article comprising an aerosol-generating substrate 12 in the form of a wrapped tobacco rod, and a mouthpiece 14 attached to the tobacco rod by a tipping wrapper 16 extending across the point of contact 18 between the downstream end of the tobacco rod and the upstream end of the mouthpiece 14.

Figure 2:
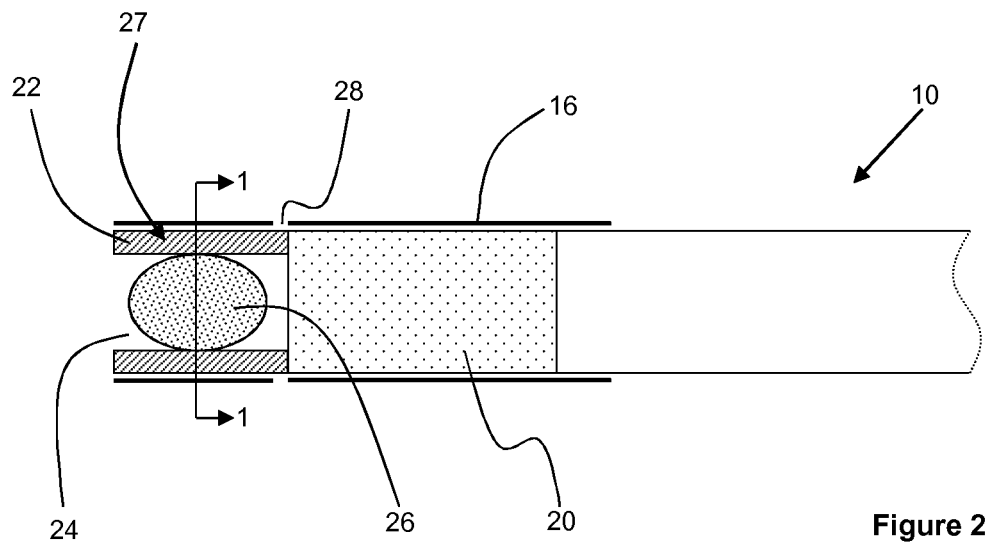
FIG. 2 shows a longitudinal cross-sectional view of the aerosol-generating article of FIG. 1.

As shown more clearly in FIG. 2, the mouthpiece 14 comprises an upstream segment of filter material 20 and a downstream segment of support material 22. The segment of support material 22 has an annular shape defining a channel 24 extending through the segment of support material 22 between its upstream and downstream ends. Contained within the channel 24 is a freshener delivery element 26 comprising a breakable capsule containing a liquid flavourant, such as parsley oil. The segment of support material 22 in combination with the freshener deliver element 26 forms a vented segment 27.

Figure 3:
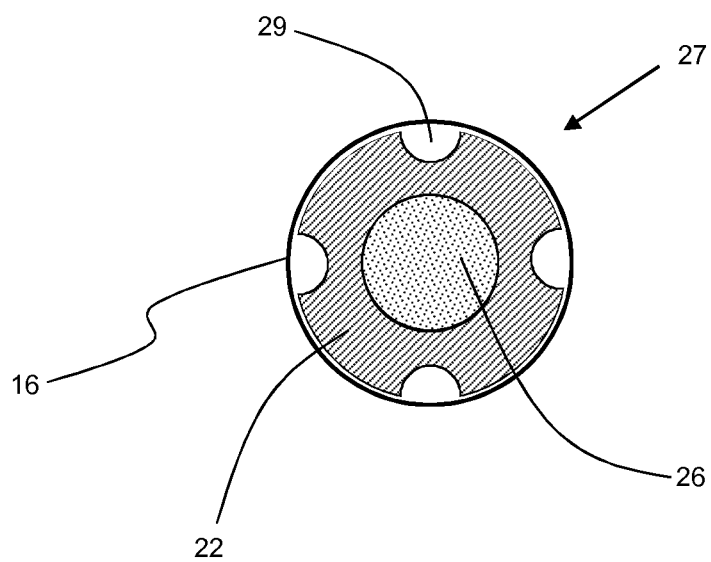
FIG. 3 shows a cross-sectional view along line 1-1 in FIG. 2.

The tipping wrapper 16 comprises a line of ventilations holes 28 extending around the full circumference of the tipping wrapper 16 and overlying the upstream edge of the segment of support material 22. The line of ventilation holes 28 communicate with a plurality of ventilation channels 29 in the surface of the segment of support material 22. The ventilation channels 29 are shown in FIG. 3, which represents a cross-sectional view of the vented segment 27 along line 1-1 of FIG. 2. The ventilation channels 29 extend between the line of ventilation holes 28 and the downstream end of the segment of support material 22 so that, with the vented segment 27 attached to the aerosol-generating article 10, the line of ventilation holes 28 and the ventilation channels 29 provides a high amount of ventilation if a consumer draws on the downstream end of the smoking article.

Figure 4:
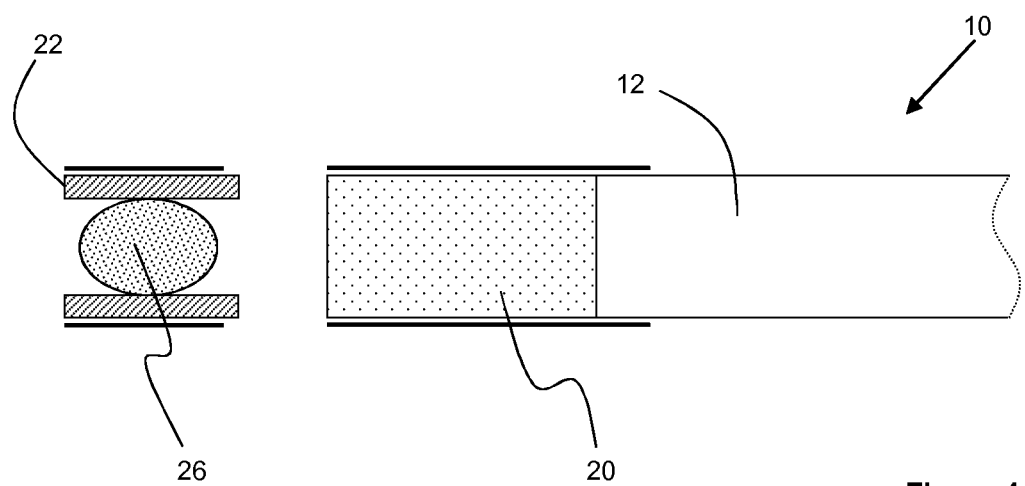
FIG. 4 shows a longitudinal cross-sectional view of the aerosol-generating article of FIG. 2 after the vented segment has been detached.

To smoke the smoking article a consumer pulls or twists the vented segment 27 relative to the segment of filter material 20 to break the tipping wrapper 16 along the line of ventilation holes 28, as shown in FIG. 4. The consumer can then smoke the smoking article comprising the tobacco rod and the segment of filter material 20 in the same manner as a conventional filter cigarette. After smoking the smoking article, the consumer can squeeze the freshener delivery element 26 along the channel 24 and out of the segment of support material 22 and consume the liquid flavourant contained within the breakable capsule.

Figure 5:
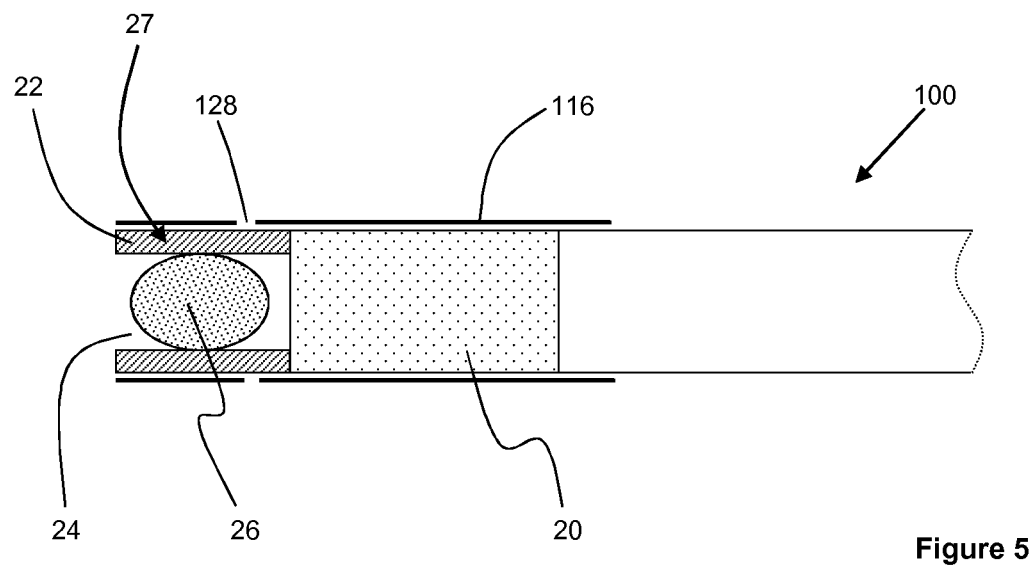
FIG. 5 shows a longitudinal cross-sectional view of an aerosol-generating article in accordance with a second embodiment of the present invention.
Figure 6:
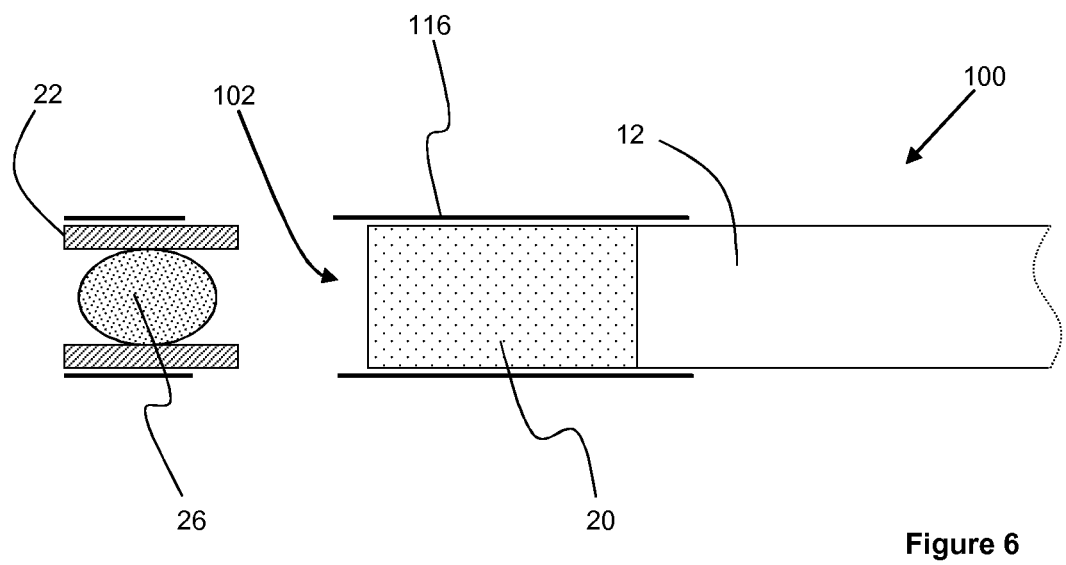
FIG. 6 shows a longitudinal cross-sectional view of the aerosol-generating article of FIG. 5 after the vented segment has been detached.

FIGS. 5 and 6 show an aerosol-generating article 100 in accordance with a second embodiment of the present invention. The aerosol-generating article 100 shown in FIGS. 5 and 6 is substantially the same as the aerosol-generating article 10 shown in FIGS. 1 to 4, and like reference numerals are used to refer to like parts.

The difference in the aerosol-generating article 100 in accordance with the second embodiment of the present invention is the tipping wrapper 116, which comprises a line of ventilation holes 128 positioned further downstream when compared to the line of ventilation holes 28 on the aerosol-generating article 10 according to the first embodiment of the present invention. Although the detachment of the vented segment 27 along the line of ventilation holes 128 functions in the same way, the position of the line of ventilation holes 128 further downstream is such that the portion of the tipping wrapper 116 that remains attached to the segment of filter material 20 extends downstream of the downstream edge of the segment of filter material 20 and therefore forms a mouth end recess 102 at the mouth end of the aerosol-generating article 100, as shown in FIG. 6.

The embodiments and examples shown in FIGS. 1 to 6 and described above illustrate but do not limit the invention. Other embodiments of the invention may be made without departing from the scope thereof, and it is to be understood that the specific embodiments described herein are not limiting.

The invention claimed is:

1. An aerosol-generating article comprising an aerosol-generating substrate and a mouthpiece secured to a downstream end of the aerosol-generating substrate, the mouthpiece comprising:

at least one segment of filter material; and a vented segment downstream of the at least one segment of filter material and comprising at least one freshener delivery element;

wherein the vented segment comprising the at least one freshener delivery element is detachable from the at least one segment of filter material to decrease ventilation of the aerosol-generating article, wherein the vented segment is at a downstream end of the mouthpiece, and wherein detachment of the vented segment results in an increase in resistance to draw of the aerosol generating article.

2. An aerosol-generating article according to claim 1, wherein the ventilation of the aerosol-generating article is at least 90 percent when the vented segment is attached to the at least one segment of filter material.

3. An aerosol-generating article according to claim 1, wherein the ventilation of the aerosol-generating article is less than 90 percent after the vented segment has been detached from the at least one segment of filter material.

4. An aerosol-generating article according to claim 1, further comprising a wrapper circumscribing the mouthpiece and a portion of the downstream end of the aerosol-generating substrate, the wrapper comprising at least one ventilation hole for admitting ambient air through the wrapper and into the vented segment.

5. An aerosol-generating article according to claim 4, wherein the wrapper comprises a line of weakness along which the vented segment is detachable from the at least one segment of filter material.

6. An aerosol-generating article according to claim 5, wherein the at least one ventilation hole comprises a line of ventilation holes, and wherein the line of ventilation holes forms the line of weakness.

7. An aerosol-generating article according to claim 5, wherein the line of weakness overlies an upstream edge of the vented segment.

8. An aerosol-generating article according to claim 5, wherein the line of weakness overlies the vented segment downstream of an upstream edge of the vented segment, and wherein a portion of the wrapper upstream of the line of weakness extends downstream of a downstream edge of the at least one segment of filter material so that the portion of the wrapper upstream of the line of weakness defines a mouth end recess when the vented segment has been detached.

9. An aerosol-generating article according to claim 1, wherein the vented segment comprises a segment of support material in which the freshener delivery element is provided.

10. An aerosol-generating article according to claim 9, wherein the segment of support material comprises one or more ventilation channels formed in a surface of the segment of support material.

11. An aerosol-generating article according to claim 9, wherein the segment of support material has an annular shape defining a channel extending through at least part of the segment of support material between an upstream end of the segment of support material and a downstream end of the segment of support material, and wherein the at least one freshener delivery element is contained within the channel extending through at least part of the segment of support material.

12. An aerosol-generating article according to claim 11, wherein each of the channel and the freshener delivery element has a substantially circular cross-sectional shape, and wherein an internal diameter of the channel is less than an external diameter of the freshener delivery element.

13. An aerosol-generating article according to claim 1, wherein the at least one freshener delivery element comprises at least one solid freshener delivery element.

14. An aerosol-generating article according to claim 1 wherein the at least one freshener delivery element comprises at least one breakable capsule containing a gel or liquid freshener.

15. An aerosol-generating article according to claim 1, wherein the at least one freshener delivery element comprises a flavourant comprising at least one of menthol, linalool, thymol, eucalyptol, methyl salicylate, and combinations thereof.

* * * * *